(12) United States Patent
Wallach et al.

(10) Patent No.: US 8,338,567 B2
(45) Date of Patent: Dec. 25, 2012

(54) PHARMACEUTICAL COMPOSITIONS FOR TREATING DISEASES ASSOCIATED WITH NF-κB ACTIVITY

(75) Inventors: David Wallach, Rehovot (IL); Parameswaran Makrishnan, Kerala (IN); Taisa Shmushkovich, Rehovot (IL)

(73) Assignee: Yeda Research and Development Co., Ltd., Rehovot (IL)

( * ) Notice: Subject to any disclaimer, the term of this patent is extended or adjusted under 35 U.S.C. 154(b) by 747 days.

(21) Appl. No.: 11/722,898

(22) PCT Filed: Dec. 11, 2005

(86) PCT No.: PCT/IL2005/001335
§ 371 (c)(1),
(2), (4) Date: Mar. 24, 2008

(87) PCT Pub. No.: WO2006/070348
PCT Pub. Date: Jul. 6, 2006

(65) Prior Publication Data
US 2009/0098106 A1 Apr. 16, 2009

(30) Foreign Application Priority Data
Dec. 27, 2004 (IL) .......................................... 166006

(51) Int. Cl.
*C07K 1/00* (2006.01)
(52) U.S. Cl. ...................................................... 530/350
(58) Field of Classification Search .................... None
See application file for complete search history.

(56) References Cited

U.S. PATENT DOCUMENTS
5,854,003 A 12/1998 Rothe et al.

FOREIGN PATENT DOCUMENTS
WO WO 99/43704 9/1999
WO WO 03/087380 * 10/2003

OTHER PUBLICATIONS

Baeuerle, et al., "NF-κB: Ten Years After", *Cell*, vol. 87, pp. 13-20, Oct. 1996.
Barnes, et al., "Nuclear Factor-κB—A Pivotal Transcription Factor in Chronic Inflammatory Diseases", *The New England Journal of Medicine*, vol. 336, pp. 1066-1071, Apr. 1997.
Behl, et al., Abstract only, "Mechanism of amyloid beta protein induced neuronal cell death: current concepts and future perspectives", *Journal of Neural Transmission Supplementum*, vol. 49, pp. 125-134, 1997.
Bose, et al., "Phosphorylation of 20S proteasome alpha subunit C8 (α7) stabilizes the 26S proteasome and plays a role in the regulation of proteasome complexes by γ-interferon", *Biochem. J.*, vol. 378, pp. 177-184, 2004.
Brand, et al., "Activated Transcription Factor Nuclear Factor-Kappa B is Present in the Atherosclerotic Lesion", *J. Clin. Invest.*, vol. 97, No. 7, pp. 1715-1722, Apr. 1996.
Brand, et al., "Dysregulation of Monocytic Nuclear Factor-κ-B by Oxidized Low-Density Lipoprotein", *Arteriosclerosis, Thrombosis, and Vascular Biology*, vol. 17, pp. 1901-1901, 1997.
Castano, et al., "Phosphorylation of C8 and C9 Subunits of the Multicatalytic Proteinase by Casein Kinase II and Identification of the C8 Phosphorylation Sites by Direct Mutagenesis", *Biochemistry*, vol. 35, pp. 3782-3789, 1996.
Gerards, et al., "Structure and assembly of the 20S proteasome", *Cell. Mol. Life Sci.*, vol. 54, pp. 253-262, 1998.
Ghosh, et al., "NF-κB and REL Protein: Evolutionarily Conserved Mediators of Immune Responses", *Annu. Rev. Immunol.*, vol. 16, pp. 225-260, 1998.
Ghosh, et al., "Missing Pieces in the NF-κB Puzzle", *Cell*, vol. 109, pp. S81-S96, Apr. 2002.
Hershko, et al., "The Ubiquitin System", *Annu. Rev. Biochem.*, vol. 67, pp. 425-479, 1998.
Kaltschmidt, et al., Abstract only, "Transcription factor NF-κB is activated in microglia during experimental autoimmune encephalomyelitis", *Journal of Neuroimmunology*, vol. 55, issue 1, pp. 99-106, Nov. 1994.
Luque, et al., "Rel/NF-κB and IκB factors in oncogenesis", *Seminars in Cancer Biology*, vol. 8, pp. 103-111, 1997.
Malinin, et al., "MAP3K-related kinase involved in NF-κB induction by TNF, CD95 and IL-1", *Nature*, vol. 385 pp. 540-544, Feb. 1997.
Mason, et al., "Phosphorylation of proteasomes in mammalian cells Identification of two phosphorylated subunited and the effect of phosphorylation on activity", *Eur. J. Biochem.*, vol. 238, pp. 453-462, 1996.
Ramakrishnan, et al., "Receptor-Specific Signaling for Both the Alternative and the Canonical NF-κB Activation Pathways by NF-κB-Inducing Kinase", *Immunity*, vol. 21, pp. 477-489, Oct. 2004.
Remick, Daniel G., "Applied Molecular Biology of Sepsis", *Journal of Critical Care*, vol. 10, No. 4, pp. 198-212, 1995.
Ruland, et al., "From antigen to activation: specific signal transduction pathways linking antigen receptors to NF-κB", *Seminars in Immunology*, vol. 15, pp. 177-183, 2003.
NCIB, "Proteasome subunit alpha type-3 isoform 1 [*Homo sapiens*]", REFSEQ accession # NP_002779.1 (retrieved May 9, 2012).
Gao, Youhe et al., "Inhibition of ubiquitin-proteasome pathway-mediated IκBα degradation by a naturally occurring antibacterial peptide", *Journal of Clinical Investigation*, vol. 106, No. 3, pp. 439-448, 2000.
Hu, Wen-Hui et al., "Activation of NF-κB by FADD, Casper, and Caspase-8*", *Journal of Biological Chemistry*, vol. 275, No. 15, pp. 10838-10844, 2000.
Horie, Rouichi et al., "Cytoplasmic Aggregation of TRAF2 and TRAF5 Proteins in the Hodgkin-Reed-Sternberg Cells", *American Journal of Pathology*, vol. 160, No. 5, 2002.
Wallach, *H.sapiens* mRNA for serine/threonine protein kinase, NIK, Genbank Y10256.1, submitted Dec. 23, 1996.
NCBI Annotation Project, *Homo sapiens* proteasome (prosome, macropain) subunit, alpha type, 3 (PSMA3), mRNA, Genbank XM_050947.1, submitted Oct. 11, 2001.

* cited by examiner

*Primary Examiner* — Sheridan Swope
(74) *Attorney, Agent, or Firm* — Browdy and Neimark, P.L.L.C.

(57) ABSTRACT

A method of treating a disease associated with NF-κB activity. The method is effected by providing to a subject in need thereof a therapeutically effective amount of an agent capable of modulating NIK-HC8 binding.

2 Claims, 11 Drawing Sheets

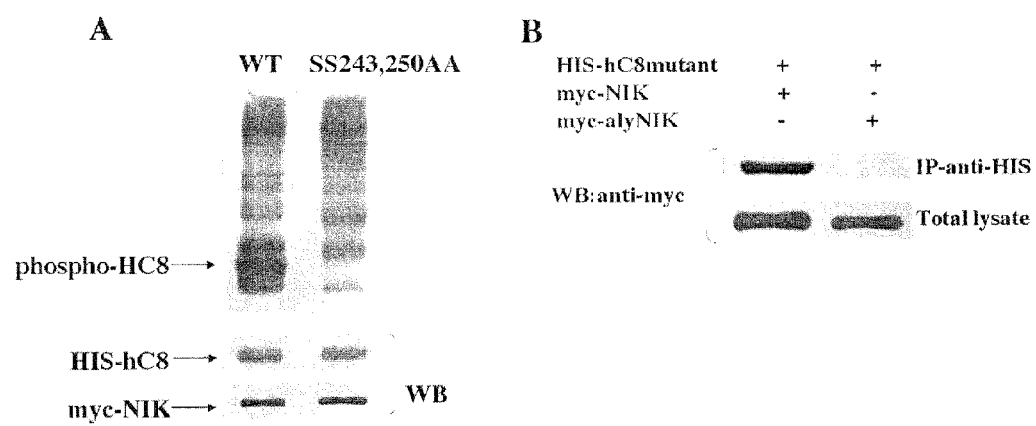
Figure 2a-b

PHARMACEUTICAL COMPOSITIONS FOR TREATING DISEASES ASSOCIATED WITH NF-κB ACTIVITY

FIELD OF THE INVENTION

The present invention relates to agents for modulating NIK binding to HC8 and methods of using such agents for treating diseases associated with NF-κB activity, such as cancer.

BACKGROUND OF THE INVENTION

The degradation of most proteins in eukaryotic cells is carried out by the ubiquitin-dependent 26S proteasome. The 26S proteasome is involved in many different cellular processes, ranging from cell-cycle regulation to antigen processing [Hershko and Ciechanover (1998) Annu. Rev. Biochem. 67:425-479]. The proteasome is composed of two large units: the 20S catalytic core complex and the 19S regulatory complex [Gerards (1998) Cell. Mol. Life Sci. 54:253-262]. The 19S complex is required for the recognition of poly-ubiquitinated protein substrates which are degraded inside the 20S complex. The barrel-shaped 20S particle is made up of four rings, each of which contains seven different subunits. The two inner rings contain β-type subunits and the outer rings comprise α-type subunits.

Two of the α-subunits of the 20S proteasome, HC8 (α7) and HC9 (α3) are known to be phosphorylated in mammalian cells. Protein kinase CK2 (casein kinase II), which is co-purified with 20S proteasome preparations, has been shown to phosphorylate HC8 at two serine residues, Ser243 and Ser250, which are localized in the C-terminus of the HC8 subunit [Mason (1996) Eur. J. Biochem. 238:453-462; Castano (1996) Biochemistry 35:3782-3789]. Recently, Bose et al. [Biochem J. (2004) 378:177-84] uncovered that treatment of cells with γ interferon resulted in the dephosphorylation of HC8 subunit and destabilization of the 26S proteasome.

The NF-κB/Rel family of transcription factors participate in inflammatory and immune cell responses, cell cycle regulation, differentiation and protection from apoptosis [Baeuerle and Baltimore, Cell 87:13-20, (1996); Ghosh, et al., Annu. Rev. Immunol. 16:225-260, (1998)]. In mammals, this family of transcription factors is comprised of five members: p65 (RelA), RelB, c-Rel, NF-κB1 (which occurs both as a precursor, p105, and in a processed form, p50) and NF-κB2 (which occurs both as a precursor, p100, and as its processed product, p52). The NF-κB protein homo- and heterodimers exist in the cytoplasm, in complex with inhibitors of the IκB family. The precursor forms of NF-κB1 and NF-κB2 (p105 and p100, respectively) contain C-terminal IκB-homologous inhibitory regions. Dimers containing these NF-κB proteins are retained in the cytoplasm by virtue of the function of the IκB-homologous regions. Moreover NF-κB1/p105 and NF-κB2/p100 can also associate with dimers of other NF-κB proteins and impose cytoplasmic retention on them. NF-κB activation occurs mainly through induced degradation of the IκB proteins or of IκB homologous regions in NF-κB1/p105 and NF-κB2/p100, and consequent translocation of the NF-κB dimers to the nucleus [Ghosh and Karin, (2002) cell S81-96].

Because of its role in inflammatory and immune cell responses, cell cycle regulation, differentiation and protection from apoptosis, activation of NF-κB plays an important role in the development of different diseases such as inflammatory diseases such as rheumatoid arthritis, asthma and inflammatory bowel disease; autoimmune diseases such as systemic lupus erythematosis; or different types of cancer [Ruland, and Mak, Semin. Immunol. 15:177-83, (2003)]. Thus, considerable efforts have been made towards uncovering agents capable of modulating NF-κB activity for use in treating NF-κB related diseases. Accordingly, a large number of molecules with immunosuppressive and anti-inflammatory properties have been studied as inhibitors of NF-κB. These include glucocorticoids and other steroid hormones, cyclosporine A, FK506, rapamycin, salicylates and gold compounds. However, the majority of these compounds have broad range of activities which often result in sever immunosuppression and other severe adverse effects.

The present inventors have previously shown that NF-κB inducing kinase (NIK) plays a central role in NF-κB activation via the canonical and alternative pathways (Ramakrishnan et al., Receptor-specific signaling for both the alternative and the canonical NF-κB activation pathways by NF-κB-inducing kinase (NIK), Immunity 21: 477-489, 2004).

While reducing the present invention to practice, the present inventors unexpectedly uncovered that NIK binds the 26S proteasomal subunit HC8 thereby activating phosphorylation of the latter. Thus, the present inventors propose that agent capable of modulating the NIK-HC8 interaction can be used to activate or suppress proteasome activity and/or NIK degradation and as a result regulate NF-κB levels thereby facilitating treatment of diseases which are associated with NF-κB activity.

SUMMARY OF THE INVENTION

According to one aspect of the present invention there is provided a method of treating a disease associated with NF-κB activity. The method is effected by providing to a subject in need thereof a therapeutically effective amount of an agent capable of modulating NIK-HC8 binding.

According to another aspect of the present invention there is provided an antibody or antibody fragment capable of disrupting a NIK-HC8 complex or preventing formation thereof.

According to yet another aspect of the present invention there is provided a method of treating a disease associated with abnormal activity of the 26S proteasome. The method is effected by providing to a subject in need thereof a therapeutically effective amount of an agent capable of decreasing NIK-HC8 binding.

According to still another aspect of the present invention there is provided a method of identifying a drug candidate suitable for treating a disease associated with NF-κB activity or an abnormal proteasome activity. The method is effected by identifying a molecule capable of modulating NIK-HC8 binding, the molecule being the drug candidate.

According to still another aspect of the present invention there is provided an isolated polypeptide comprising no more than 200 amino acids and including the amino acid sequence set forth by coordinates 1-180 or 650-947 of SEQ ID NO: 5, the isolated polypeptide being capable of disrupting a NIK-HC8 complex or preventing formation thereof.

According to further features in preferred embodiments of the invention described below, the modulating NIK-HC8 binding is effected by disrupting a NIK-HC8 complex or preventing formation thereof.

According to still further features in the described preferred embodiments the agent is an oligonucleotide complementary to an endogenous nucleic acid sequence encoding the HC8 or NIK.

According to still further features in the described preferred embodiments the agent is an antibody or an antibody fragment.

According to still further features in the described preferred embodiments an antigen recognition domain of the antibody or fragment thereof is encompassed by amino acids 1-180 or 650-947 of the amino acid sequence set forth by SEQ ID NO: 5.

According to still further features in the described preferred embodiments the agent is a peptide including an HC8-derived amino acid sequence capable of binding NIK, the peptide being at least 5 and no more than 50 amino acids in length.

According to still further features in the described preferred embodiments the modulating NIK-HC8 binding is effected by stabilizing a NIK-HC8 complex or enhancing formation thereof.

According to still further features in the described preferred embodiments the agent is a polynucleotide capable of expressing at least an active portion of NIK or HC8.

According to still further features in the described preferred embodiments the agent is a polypeptide including at least an active portion of NIK or HC8.

According to still further features in the described preferred embodiments the agent is a NIK inhibitor.

According to still further features in the described preferred embodiments the disease associated with NF-κB activity is an immune disease, an inflammatory disease or a cancer.

According to still further features in the described preferred embodiments the agent is selected from the group consisting of a molecule capable of inhibiting a kinase activity of NIK, a non-phosphorylated mutant of HC8 and a non functional derivative of NIK.

According to still further features in the described preferred embodiments the molecule is selected from the group consisting of a small molecule chemical, a polynucleotide, an oligonucleotide, an aptamer, a polypeptide, a peptide and an antibody.

The invention also provides for the use of an agent capable of modulating NIK-HC8 binding in the preparation of a medicament for treatment of a disease associated with NF-κB activity.

The present invention successfully addresses the shortcomings of the presently known configurations by providing agents for modulating the NIK-HC8 interaction and methods of using same for treating diseases associated with NF-κB activity, such as cancer.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 2a-b show Western blot analyses of immunoprecipitation assays illustrating phosphorylation of HC8 by NIK. FIG. 2a—Wild type (WT) HIS-tagged HC8 or SS243,250AA mutated HIS-tagged HC8 were co-expressed with myc-tagged NIK in 293T cells. Immunoprecipitation was effected using anti-HIS antibodies to precipitate HC8 and NIK bound thereto. Immunoprecipitates were incubated with 5 μci of $\gamma^{32}P$ ATP in kinase reaction buffer for 30 min at 30° C. Samples were resolved on 12% SDS-PAGE, transferred to a nitrocellulose membrane and visualized by autoradiography. The membrane was later probed with anti-HIS and anti-myc antibodies. Lower panel shows the amount of immunoprecipitated wild type and mutant HC8 along with NIK. FIG. 2b shows co-immunoprecipitation of NIK, but not aly NIK, with mutant HC8. Expression levels of NIK and aly NIK in total cell lysates are shown in the lower panel.

FIG. 3a shows presence of C8-binding motif(s) upstream of the C-terminal region of NIK. FIG. 3b illustrates that the kinase domain does not bind HC8. FIG. 3c illustrates a NIK-HC8 binding region downstream of amino acid 187 of NIK. FIGS. 3d-g illustrates NIK-HC8 binding region(s) downstream of amino acid 180 of NIK.

3d. Co-immunoprecipitation of HIS tagged NIK C-terminal deletions and myc tagged hC8. 1 was transfected with HIS-NIK 1-237 and hC8-myc and 2 was transfected with HIS-NIK 1-367 and hC8-myc. Immunoprecipitation was carried out with anti-myc antibody and the blot was probed with anti-HIS antibody to detect co precipitating NIK fragment. NIK1-237 was poorly expressed and therefore its binding to hC8 is not conclusive. NIK 1-367 binds to hC8. The two left lanes show immunoprecipitations and two right lanes show amount of NIK expressed in total lysates.

3e. Co-immunoprecipitation of HIS tagged NIK C-terminal deletions and myc tagged hC8. 1 was transfected with HIS-NIK 1-180 and hC8-myc, 2 was transfected with HIS-NIK 1-201 and hC8-myc and 3 was transfected with HIS-NIK 1-220 and hC8-myc. Immunoprecipitation was carried out with anti-myc antibody and the blot was probed with anti-HIS antibody to detect co precipitating NIK fragment. The three left lanes show immunoprecipitations and three right lanes show amount of NIK expressed in total lysates. All three fragments of NIK co-precipitated with hC8.

3f. Co-immunoprecipitation of HIS tagged NIK N-terminal deletions and myc tagged hC8. 1 was transfected with HIS-NIK 238-947 and hC8-myc, 2 was transfected with HIS- NIK 251-947 and hC8-myc, 3 was transfected with HIS-NIK 281-947 and hC8-myc, 4 was transfected with HIS-NIK321-947 and hC8-myc and 5 was transfected with HIS-NIK 368-947 and hC8-myc. Immunoprecipitation was carried out with anti-myc antibody and the blot was probed with anti-NIK antibody to detect co-precipitating NIK fragment. The five left lanes show immunoprecipitations and five right lanes show amount of NIK expressed in total lysates. All five fragments of NIK co-precipitated with hC8. However, the binding of NIK 321-947 and NIK 368-947 to hC8 was found reduced.

3g. Co-immunoprecipitation of HIS tagged NIK N-terminal deletions and myc tagged hC8. 1 was transfected with pc DNA3 empty vector and hC8-myc, 2 was transfected with HIS-NIK 259-947 and hC8-myc, 3 was transfected with HIS-NIK 281-947 and hC8-myc, 4 was transfected with HIS-NIK 305-947 and hC8-myc and 5 was transfected with HIS-NIK 321-947 and hC8-myc. Immunoprecipitation was carried out with anti-myc antibody and the blot was probed with anti-NIK antibody to detect co-precipitating NIK fragment. The five left lanes show immunoprecipitations and five right lanes show amount of NIK expressed in total lysates. All five fragments of NIK co-precipitated with hC8. Sample number 1 served as a negative control for NIK overexpression.

Figure 4:
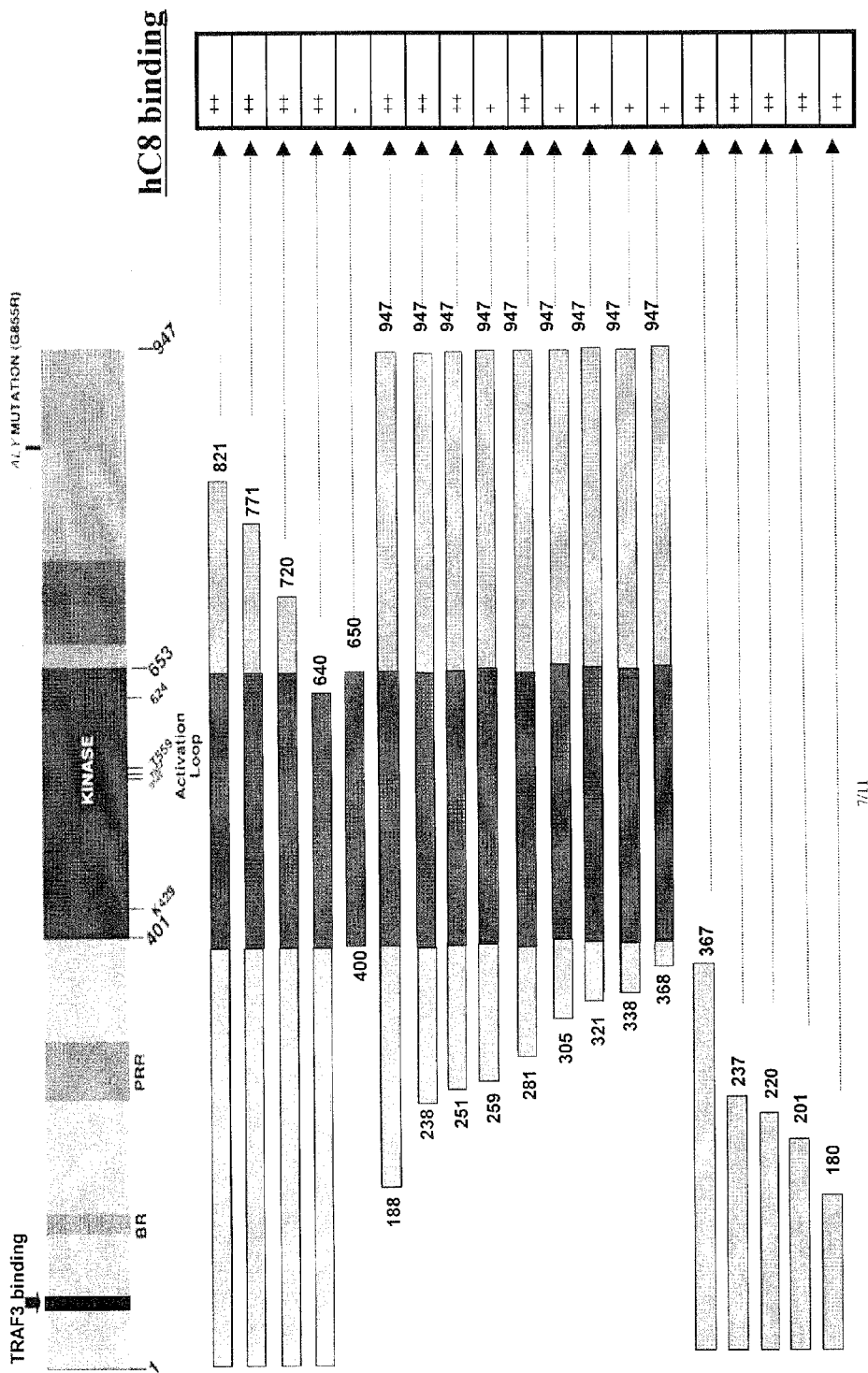

FIG. 4 is a diagram summarizing deletion analyses of NIK regions capable of binding to HC8. The diagram illustrates at least two binding regions for HC8 in NIK: one binding region within amino acids 1-180 at the N-terminus, and another binding region within the C terminus (amino acids 650-947). The diagram further shows that there no binding region was identified within the kinase motif of NIK (amino acids 400-650).

Figure 5:
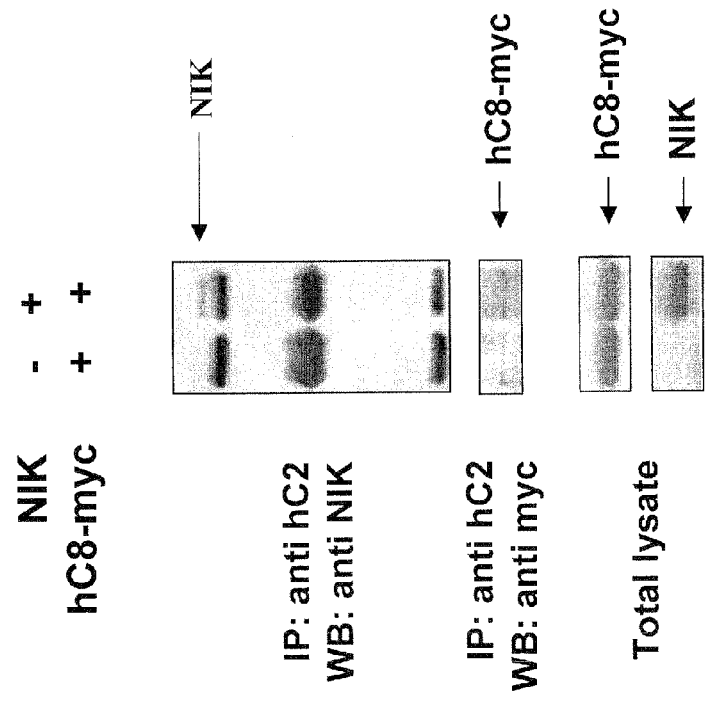

FIG. 5 shows Western blot analyses of immunorecipitation assays illustrating that the NIK-HC8 binding occurs with proteasome-associated HC8 (and not with free HC8). Myc-tagged HC8 and His-tagged NIK were transiently expressed in HeLa cells. Proteaosomes were precipitated from cell lysates using anti C2 proteasomal-component antibody. The analyses show co-precipitation of both tagged HC8 and NIK molecules with C2.

Figure 6:
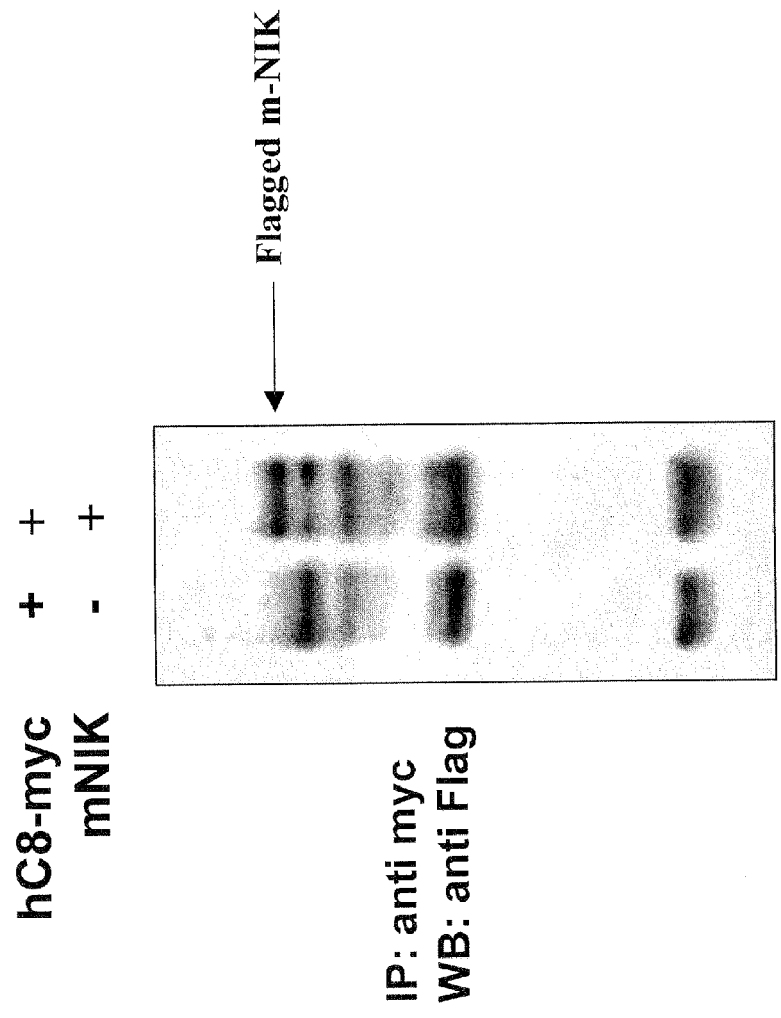

FIG. 6 shows Western blot analyses of immunorecipitation assays illustrating that mouse NIK also binds to human C8 (HC8). Full-length mouse NIK and various deletion mutants thereof (with the indicated N- and C-terminal residues), linked to the FLAG-tag, were transiently co-expressed in HeLa cells with HC8 fused either to the Flag or Myc tag. The mouse NIK and HC8 association was assessed by immunoprecipitation of NIK from the cell lysates using anti-NIK monolclonal antibody followed by Western analysis.

Figure 7:
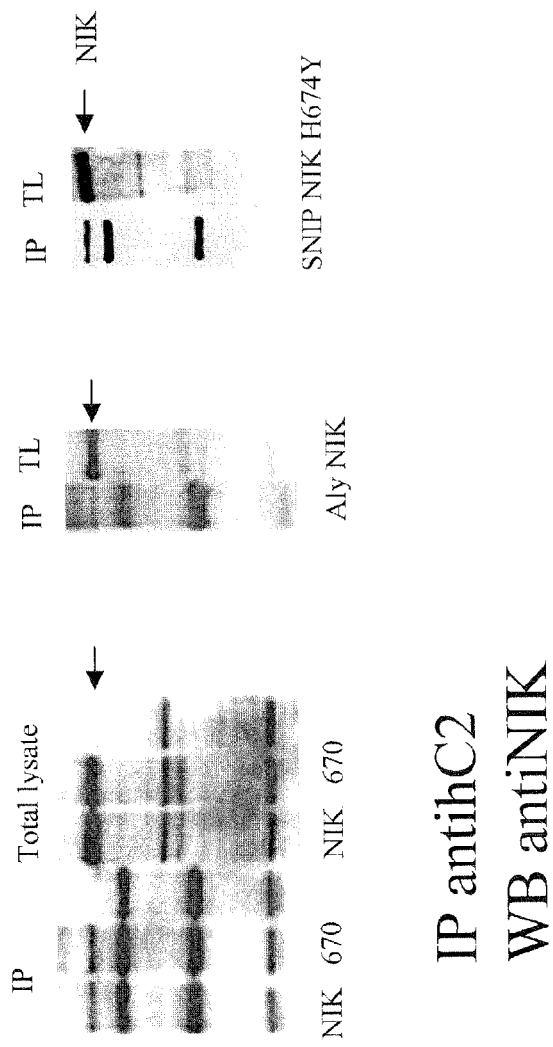

FIG. 7 shows Western blot analyses of immunorecipitation assays illustrating that aly mutation, replacement of lysine 670 with alanine, and a naturally occurring single nucleotide polymorphic variation of NIK (H674Y) do not prevent NIK binding to the proteasome. Myc-tagged HC8 and His-tagged NIK were transiently expressed in HeLa cells, Proteaosomes were precipitated from the cell lysates using anti C2 proteasomal component antibody.

Figure 8:
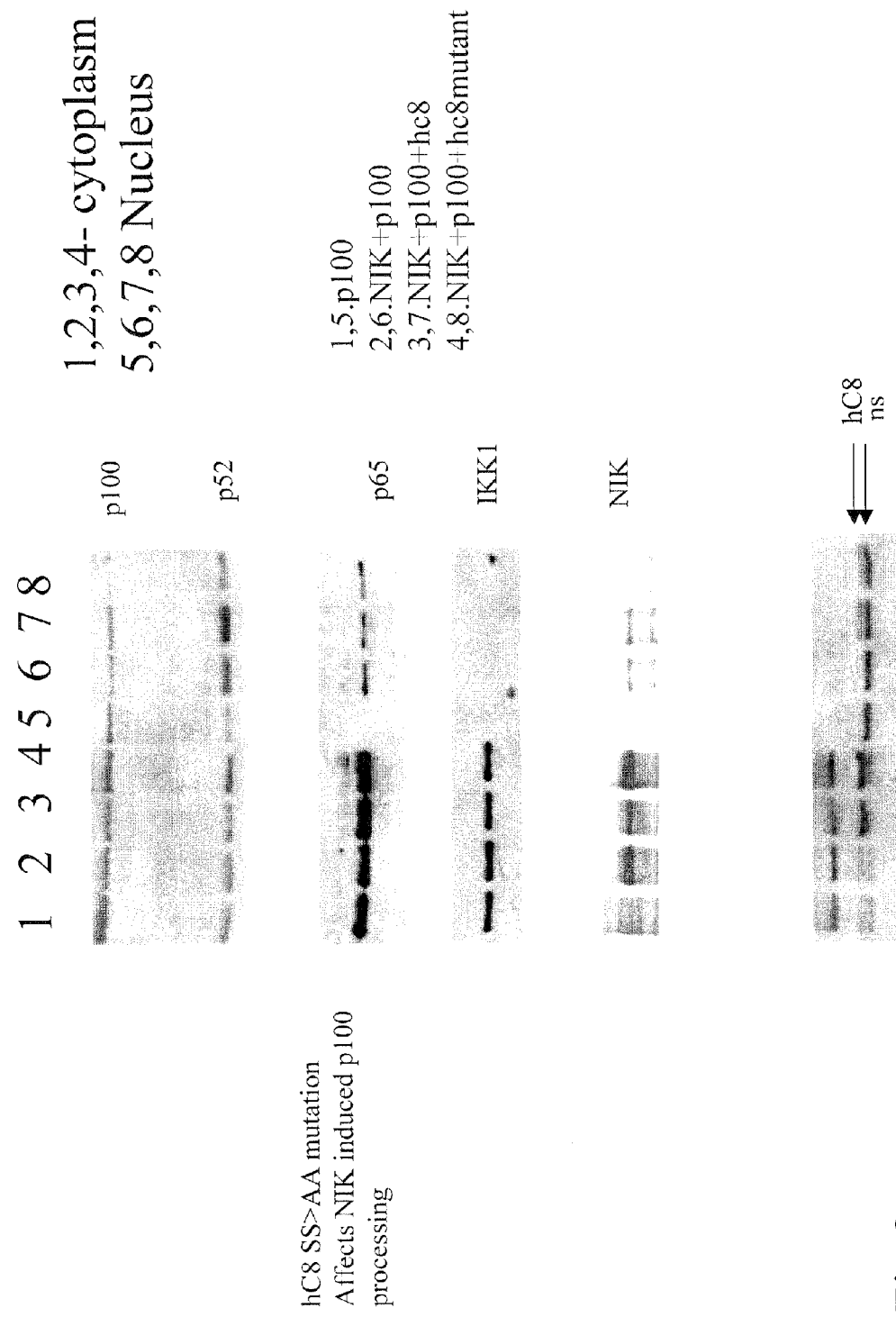

FIG. 8 shows Western blot analyses of immunorecipitation assays illustrating the effect of mutating serine residues 243 and 250 in HC8 (NIK phosphorylation sites) on NIK-induced alternative NF-κB pathway and nuclear translocation of HC8 and NIK. Human NIK and HC8 having serine residues 243 and 250 replaced by alanine were co-expressed with NIK and NF-κB (p100) in HeLa cells. Following 25 hr incubation, the nuclei and cytoplasmic fractions of the cells were isolated and probed for p52 (indicative of p100 processing induced via activation of the alternative pathway), NF-κB p65, NIK and HC8. The analyses show a substantial decrease of p52 in cells co-expressing mutated HC8. In addition, the analyses show translocation of NIK and HC8 to nuclei of cells co-expressing wild-type HC8 but not to nuclei of cells co-expressing mutated HC8.

DESCRIPTION OF THE PREFERRED EMBODIMENTS

The present invention is of a method of treating diseases associated with NF-κB activity. Specifically, the present invention relates to methods of regulating NF-κB activity by modulating the NIK—with HC8 interaction.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

NF-κB inducing kinase (NIK) is a serine/threonine kinase which is capable of stimulating NF-κB activity (Malinin et al., Nature 385: 540-544, 1997). Initial studies showed that NIK induces proteolytic processing of NF-κB2/p100 and hence the generation of NF-κB dimers such as p52; RelB. Recently, Ramakrishnan et al. (Immunity 21: 477-489, 2004) showed that NIK participates in a unique set of proximal signaling events, initiated by specific inducers, which activate NF-κB dimers.

While reducing the present invention to practice the present inventors surprisingly and unexpectedly uncovered that NIK is capable of binding the C8 (HC8) subunit of the human 20S proteasome in mammalian cells (Example 1) and that such binding can result in activation of HC8 phosphorylation (Example 2). Since HC8 phosphorylation is associated with 26S proteasome activity (as described in the introduction section hereinabove), the present inventors have postulated that modulating the NIK-HC8 interaction could effectively stabilize or destabilize the 26 proteasome and consequently increase or decrease proteasome mediated degradation of NIK (which is necessary for NF-κB activity, as described hereinabove) and/or degradation of NF-κB precursors (e.g., p100).

Thus, according to one aspect of the present invention there is provided a method of treating a disease associated with NF-κB activity. The method is effected by providing to a subject in need thereof a therapeutically effective amount of an agent capable of modulating NIK-HC8 binding.

As used herein the phrase "a subject in need thereof" refers to a mammal, preferably a human subject, having a disease associated with NE-κB activity or is at a risk of developing a disease associated with NF-κB activity (i.e., predisposed).

As used herein the term "treating" refers to reversing, alleviating, inhibiting the progress of, or preventing the disease, disorder or condition to which such term applies, or one or more symptoms of such disorder or condition. The term "treatment" or "therapy" refer to the act of treating the subject.

A disease associated with NF-κB activity can be any disease, disorder or condition which is induced, enhanced or suppressed by NF-κB activity. Diseases associated with NF-κB activity include, but are not limited to, immune diseases (e.g., systemic lupus erythematosis), inflammatory diseases (e.g., rheumatoid arthritis, asthma and inflammatory bowel disease) and cancer [Parnes P. J., N Engl J. Med. 336:1066-1071, 1997; Brand, et al., J Clin Invest. 97: 1715-1722, 1996; Remick D G. J Crit Care. 10: 198-212, 1995; Behl et al., J Neural Transm Suppl. 49:125-134, 1997; Brand et al., Arterioscler Thromb Vasc Biol. 17: 1901-1909, 1997; Kaltschmidt et al., J. Neuroimmunol. 55: 99-106, 1994; Luque et al., Semin Cancer Biol. 8: 103-111, 1997; and Ruland and Mak, Semin. Immunol. 15:177-183, 2003].

As is mentioned hereinabove, the present invention enables treatment of diseases associated with reduced or elevated activity of NF-κB. In cases where the disease is associated with a reduction of NF-κB activity (e.g., various types of immune deficiencies) the subject can be treated with an agent capable of dissociating a NIK-HC8 complex or preventing formation thereof. Treatment with such agent would suppress NIK-dependent HC8 phosphorylation and thereby destabilize 26S proteasome, resulting in reduced degradation of NIK, reduced degradation of NF-κB and/or altered activation of NIK.

Such an agent can be, for example, an antibody or an antibody fragment capable of binding HC8 or NIK. Preferably, the antibody specifically binds at least one epitope of NIK or HC8. More preferably, the antibody specifically binds at least one epitope of an NIK binding site of HC8 or at least one epitope of an HC8 binding site of NIK. Most preferably, the antibody specifically binds to an antigen encompassed by amino acids 1-180 or 650-947 of the amino acid sequence set forth by SEQ ID NO: 5 and, preferably, being no more than 200 amino acids in length.

As used herein, the term "epitope" refers to any antigenic determinant on an antigen to which the paratope of an antibody binds.

Epitopic determinants are composed of chemically active surface groupings of molecules such as amino acids or carbohydrate side chains and usually have specific three dimensional structural characteristics, as well as specific charge characteristics. Preferred epitopes of NIK or HC8 are those comprising the NIK-HC8 binding sites site such as, for example the NIK C-terminus or the NIK N-terminus binding sites (within amino acids 650-947 and 1-180, respectively) described in Example 2.

The term "antibody" as used herein includes intact molecules as well as functional fragments thereof, such as Fab, F(ab')2 and Fv. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to the present invention can be prepared by proteolytic hydrolysis of the antibody or by expression in E. coli or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (1972)]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (scFv) are prepared by constructing a structural gene comprising DNA sequences encoding the VH and VL domains connected by an oligonucleotide. The structural gene is inserted into an expression vector, which is subsequently introduced into a host cell such as E. coli.

The antibody utilized by the present invention is preferably an antibody fragment which is capable of being delivered to, or expressed in, mammalian cells. Thus, an scFv Ab coding sequence is preferably included in an vector suitable for expression of the NIK or HC8 scFv fragment in mammalian cells (see hereinbelow for details on expression vector construction). A suitable scFv expression vector can be, for example, pIG6 [Ge: in Antibody Engineering (Boreback C. A. K ed.) 2nd ed. pp 229-261, 1995 Oxford university], pFab5c or pcDNA3.1 is described by Khoshar (PNAS 99:1002-1007, 2002).

The recombinant host cells synthesize a single polypeptide chain with a linker peptide bridging the two V domains. Methods for producing scFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946,778.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

Humanized forms of non-human (e.g., murine) antibodies are chimeric molecules of immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321: 522-525 (1986); Riechmann et al., Nature, 332:323-329 (1988); and Presta, Curr. Op. Struct. Biol., 2:593-596 (1992)].

Methods for humanizing non-human antibodies are well known in the art, Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)], The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

The antibody of the present invention can also be generated by initially producing NIK or HC8 specific polyclonal antiserum using standard methods known in the art, as described hereinabove. Antisera aliquots are then passed through a plurality of affinity-binding columns each containing a specific amino acid portion of NIK, or HC8, so as to purify a plurality of mono-specific polyclonal antibody subsets (each subset specifically recognizes one or several NIK, or HC8 epitopes). The subsets are then screened and selected for an ability to disrupt NIK-HC8 binding or dissociate a NIK-HC8 complex in mammalian cells using methods such as those described hereinbelow.

An agent capable of preventing formation of a NIK-HC8 complex can also be a small interfering RNA (siRNA) molecule capable of suppressing expression of NIK or HC8. RNA interference is a two step process. the first step, which is termed as the initiation step, input dsRNA is digested into 21-23 nucleotide (nt) small interfering RNAs (siRNA), probably by the action of Dicer, a member of the RNase III family of dsRNA-specific ribonucleases, which processes (cleaves) dsRNA (introduced directly or via a transgene or a virus) in an ATP-dependent manner. Successive cleavage events degrade the RNA to 19-21 bp duplexes (siRNA), each with 2-nucleotide 3' overhangs [Hutvagner and Zamore Curr. Opin. Genetics and Development 12:225-232 (2002); and Bernstein Nature 409:363-366 (2001)].

In the effector step, the siRNA duplexes bind to a nuclease complex to from the RNA-induced silencing complex (RISC). An ATP-dependent unwinding of the siRNA duplex is required for activation of the RISC. The active RISC then targets the homologous transcript by base pairing interactions and cleaves the mRNA into 12 nucleotide fragments from the 3' terminus of the siRNA [Hutvagner and Zamore Curr. Opin. Genetics and Development 12:225-232 (2002); Hammond et al. (2001) Nat. Rev. Gen. 2:110-119 (2001); and Sharp Genes. Dev. 15:485-90 (2001)]. Although the mechanism of cleavage is still to be elucidated, research indicates that each RISC contains a single siRNA and an RNase [Hutvagner and Zamore Curr. Opin. Genetics and Development 12:225-232 (2002)].

Because of the remarkable potency of RNAi, an amplification step within the RNAi pathway has been suggested. Amplification could occur by copying of the input dsRNAs which would generate more siRNAs, or by replication of the siRNAs formed. Alternatively or additionally, amplification could be effected by multiple turnover events of the RISC [Hammond et al. Nat. Rev. Gen. 2:110-119 (2001), Sharp Genes. Dev. 15:485-90 (2001); Hutvagner and Zamore Curr. Opin. Genetics and Development 12:225-232 (2002)]. For more information on RNAi see the following reviews Tuschl ChemBiochem. 2:239-245 (2001); Cullen Nat. Immunol. 3:597-599 (2002); and Brantl Biochem. Biophys. Act. 1575: 15-25 (2002).

Synthesis of RNAi molecules suitable for use with the present invention can be effected as follows. First, the NIK or HC8 mRNA sequence is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl ChemBiochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (www.ambion.com/techlib/tn/91/912.html).

Second, potential target sites are compared to an appropriate genomic database (e.g., human, mouse, rat etc.) using any sequence alignment software, such as the BLAST software available from the NCBI server (www.ncbi.nlm.nih.gov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene. As example siRNA sequences which can be used to disrupt a NIK-HC8 complex or preventing formation thereof according to the teaching of the present invention is set forth in SEQ ID NOs: 1-2 (sense/antisense) and SEQ ID NOs: 3-4 (sense/antisense).

Another agent capable of preventing formation of a NIK-HC8 complex is a DNAzyme molecule capable of specifically cleaving an mRNA transcript or DNA sequence encoding NIK or HC8. DNAzymes are single-stranded polynucleotides which are capable of cleaving both single and double stranded target sequences (Breaker, R. R. and Joyce, G. Chemistry and Biology 1995:2:655; Santoro, S. W. & Joyce, G. F. Proc. Natl, Acad. Sci. USA 1997; 943:4262) A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro, S. W. & Joyce, G. F. Proc. Natl, Acad. Sci. USA 199; for rev of DNAzymes see Khachigian, L M [Curr Opin Mol Ther 4:119-21 (2002)].

Examples of construction and amplification of synthetic, engineered DNAzymes recognizing single and double-stranded target cleavage sites have been disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in vivo (Itoh et al, 20002, Abstract 409, Ann Meeting Am Soc Gen Ther www.asgt.org). In another application, DNAzymes complementary to bcr-abl oncogenes were successful in inhibiting the oncogenes expression in leukemia cells, and lessening relapse rates in autologous bone marrow transplant in cases of CML and ALL.

Preventing formation of a NIK-HC8 complex can also be effected by using an antisense polynucleotide capable of specifically hybridizing with an mRNA transcript encoding NIK or HC8.

Design of such an antisense molecules must be effected while considering two aspects important to the antisense approach. The first aspect is delivery of the oligonucleotide into the cytoplasm of the appropriate cells, while the second aspect is design of an oligonucleotide which specifically binds the designated mRNA within cells in a way which inhibits translation thereof.

The prior art teaches of a number of delivery strategies which can be used to efficiently deliver oligonucleotides into a wide variety of cell types [see, for example, Luft J Mol Med 76: 75-6 (1998); Kronenwett el al. Blood 91: 852-62 (1998); Rajur et al. Bioconjug Chem 8: 935-40 (1997); Lavigne et al. Biochem Biophys Res Commun 237: 566-71 (1997) and Aoki el al. (1997) Biochem Biophys Res Commun 231: 540-5 (1997)].

In addition, algorithms for identifying those sequences with the highest predicted binding affinity for their target mRNA based on a thermodynamic cycle that accounts for the energetics of structural alterations in both the target mRNA and the oligonucleotide are also available [see, for example, Walton et al. Biotechnol Bioeng 65: 1-9 (1999)].

Such algorithms have been successfully used to implement an antisense approach in cells. For example, the algorithm developed by Walton et al. enabled scientists to successfully design antisense oligonucleotides for rabbit beta-globin (RBG) and mouse tumor necrosis factor-alpha (TNF alpha) transcripts. The same research group has more recently reported that the antisense activity of rationally selected oligonucleotides against three model target mRNAs (human lactate dehydrogenase A and B and rat gp130) in cell culture as evaluated by a kinetic PCR technique proved effective in almost all cases, including tests against three different targets in two cell types with phosphodiester and phosphorothioate oligonucleotide chemistries.

In addition, several approaches for designing and predicting efficiency of specific oligonucleotides using an in vitro system were also published (Matveeva et al., Nature Biotechnology 16: 1374-1375 (1998)].

Several clinical trials have demonstrated safety, feasibility and activity of antisense oligonucleotides. For example, antisense oligonucleotides suitable for the treatment of cancer have been successfully used [Holmund et al., Curr Opin Mol Ther 1:372-85 (1999)], while treatment of hematological malignancies via antisense oligonucleotides targeting c-myb gene, p53 and Bcl-2 had entered clinical trials and had been shown to be tolerated by patients [Gerwitz Curr Opin Mol Ther 1:297-306 (1999)].

More recently, antisense-mediated suppression of human heparanase gene expression has been reported to inhibit pleural dissemination of human cancer cells in a mouse model [Uno et al., Cancer Res 61:7855-60 (2001)].

Thus, the current consensus is that recent developments in the field of antisense technology which, as described above, have led to the generation of highly accurate antisense design algorithms and a wide variety of oligonucleotide delivery systems, enable an ordinarily skilled artisan to design and implement antisense approaches suitable for downregulating expression of known sequences without having to resort to undue trial and error experimentation.

Yet another agent capable of preventing formation of a NIK-HC8 complex is a ribozyme molecule capable of specifically cleaving an mRNA transcript encoding a NIK or HC8. Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders [Welch et al., Clin Diagn Virol. 10:163-71 (1998)]. Most notably, several ribozyme gene therapy protocols for HIV patients are already in Phase 1 trials. More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms have demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Incorporated—WEB home page).

Synthesis of oligonucleotide molecules (e.g., siRNA, antisense etc) suitable for use with the present invention can be effected using routine methods well known in the art and are specified, for example, in P. Herdewijn, Ed., Oligonucleotide Synthesis, Humana Press, 2004.

Disrupting a NIK-HC8 complex or preventing formation thereof can also be effected using a peptide which includes an HC8-derived amino acid sequence capable of binding NIK or a NIK-derived amino acid sequence capable of binding HC8. More preferably, the peptide is a NIK-derived amino acid sequence encompassed by amino acids 650-947 or 1-180 of the amino acid sequence set forth in SEQ ID NO: 5.

As used herein, the terms "polypeptide" and "peptide" are used interchangeably and include native peptides (either degradation products, synthetically synthesized peptides or recombinant peptides) and peptidomimetics (typically, synthetically synthesized peptides), such as peptoids and semipeptoids which are peptide analogs, which may have, for example, modifications rendering the peptides more stable while in a body, or less immunogenic. Such modifications include, but are not limited to, cyclization, N-terminus modification, C-terminus modification, peptide bond modification, including, but not limited to, $CH_2$—$NH$, $CH_2$—$S$, $CH_2$—$S$=$O$, $O$=$C$—$NH$, $CH_2$—$O$, $CH_2$—$CH_2$, $S$=$C$—$NH$, $CH$=$CH$ or $CF$=$CH$, backbone modification and residue modification. Amino acid sequences of mammals HC8 (for example GeneBank Accession Number XM_050947) and NIK (for example GeneBank Accession Number Y10256) are readily accessible. Synthesis of peptide molecules suitable for use with the present invention can be effected using routine methods well known in the art and are specified, for example, in C. A. Ramsden Ed, Quantitative Drug Design, Chapter 17.2, F. Choplin Pergamon Press, 1992.

In cases where the disease is associated with an increase of NF-κB activity (e.g., Hodgkin lymphoma and many other types of cancer; chronic inflammatory diseases such as Crohn's disease and Rheumatoid Arthritis) the subject can be treated with an agent capable stabilizing a NIK-HC8 complex or enhancing formation thereof. Treatment with such agent would promote NIK-dependent HC8 phosphorylation and thereby stabilize 26S proteasome, resulting in increased degradation of NIK and/or NF-κB.

A suitable agent capable of stabilizing a NIK-HC8 complex or enhancing formation thereof can be a polynucleotide encoding NIK or HC8. Alternatively, the agent can be a polypeptide including at least an active portion of NIK or HC8 or a complex forming portion thereof.

As is mentioned hereinabove, NIK-HC8 complex formation leads to increased phosphorylation of HC8 and as a result to an increase in 26S proteasome stability and activity.

Thus, the present invention also envisages stabilizing, or destabilizing 26 proteasome by increasing or decreasing NIK-dependent HC8 phosphorylation. Agents which may be utilized for altering NIK-dependent HC8 phosphorylation include, for example, NIK mutants lacking kinase activity or NIK-HC8-targeted kinase inhibitors.

The agents of the present invention can be used in treatment of NF-κB related diseases per se or as part (active ingredient) of a pharmaceutical composition.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, inrtaperitoneal, intranasal, or intraocular injections.

Alternately, one may administer the pharmaceutical composition in a local rather than systemic manner, for example, via injection of the pharmaceutical composition directly into a bone tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. One route of administration which is suited for the pharmaceutical compositions of the present invention is sub-periosteal injection, as described in U.S. Pat. No. 6,525,030 to Erikkson. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate. As used herein, the term "oral administration" includes administration of the pharmaceutical compound to any oral surface, including the tongue, gums, palate, or other buccal surfaces. Addition methods of oral administration include provision of the pharmaceutical composition in a mist, spray or suspension compatible with tissues of the oral surface.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (e.g. antisense oligonucleotide) effective to prevent, alleviate or ameliorate symptoms of a disorder (e.g., mammary tumor progression) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to levels of the active ingredient which are sufficient to, for example, retard tumor progression in the case of blastic metastases (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

In order to facilitate practice of the methods described hereinabove, and/or production of the pharmaceutical compositions described above, the present invention further provides a method of identifying novel drug candidates for treating diseases associated with NF-κB activity and/or for treating diseases associated with abnormal proteasome activity.

The method is effected by screening a plurality of molecules, preferably a small molecule chemical, a polynucleotide, an oligonucleotide, an aptamer, a polypeptide, a peptide or an antibody, for an ability to dissociate a NIK-HC8 complex or prevent formation thereof in mammalian cells. Screening may be effected using a co-immunoprecipitation assay in lysates of cultured cells co-expressing HC8 and NIK. An exemplary screening assay is described in detail in Example 1 of the Example section hereinbelow. Alternatively, drug candidates may be screened for an ability to modulate NIK-dependent HC8 phosphorylation using an in vitro kinase assay such as described in detail in Example 2 of the Example section hereinbelow.

Once molecules capable of modulating NIK-dependent HC8 phosphorylation are identified in vitro further analysis is conducted in order to determine their cell penetration capabilities and their toxicity to mammals. If need be, suitable drug candidates are modified in order to increase cell penetration thereof and decrease toxicity without substantially affecting their activity in modulating NIK-dependent HC8 phosphorylation.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

NIK Interacts with the HC8 Subunit of the 20S Proteasome

Materials and Experimental Procedures

Constructs: NIK-pCS3MTNIK with N-terminal 6 myc tag, aly NIK, Kinase dead NIK, NIK K670A and SniP NIK H674Y constructs were generated from pCS3MTNIK by site directed mutagenesis using pfu DNA polymerase using the manufacturer's protocol (Stratagene).

HC8 was subcloned from 2 Hybrid prey into pCDNA3 vector with HIS tag in the N terminus then subcloned into PCDNA3 with an added myc tag in the C terminus.

HC8 SS 243,250AA mutant was generated by site directed mutagenesis. All NIK deletions were created either by restriction digestion in the corresponding region or by PCR amplification and cloned into pCDNA-HIS vector.

Yeast 2 Hybrid Screening Assays: NIK or its deletions were cloned into pGBKT7 vector as bait and the preys were re-cloned into pGADT7 vector for assay in the yeast strain SFY526. The system used for screening was the Matchmaker version III (clontech). The prey was pretransformed human bone marrow library (cat# HY4053AH) pooled from 51 males/females in the age range 22-70. It belongs to a new generation of 2 hybrid libraries that offers high stringent quadruple drop out (QDO) selection along with α-gal assay. Clones growing on plates without LEU, TRP, HIS and ADE were reconfirmed by α-gal assay. Plasmids of the positive clones were prepared by lysis of the yeast cells with detergent and mechanical stress followed by phenol extraction and ethanol precipitation of the DNA. Encoded inserts from the plasmids were amplified by PCR with the primers specific for the library vector pACT2.

Cells: HEK 293T and HeLa cells were used.

Transfection: Transfection was effected using the calcium phosphate precipitation method as described by Sambrook et al., (Molecular cloning. A Laboratory Manual. SE. CSH press, 1989). Briefly, 1.5 million 293-T cells were seeded into 10 cm plates. Following a 24 hr period of incubation the cultures were transfected with respective plasmids while maintaining a total DNA concentration of 15 μg per plate by adding empty vector.

Lysate Preparation and Co-Immunoprecipitation: Cells were harvested 24 hr following transfection then lysed in 1% Triton X-100 lysis buffer [(1% Triton X-100, 150 mM NaCl, 1 mM EDTA, 20 mM Tris-cl (pH 7.6) and 1× complete protease inhibitor (Roche)]. All immunoprecipitations were carried out by incubation for 4 hours at 4° C. with the respective antibodies and protein G sepharose beads (Amersham Pharmacia).

Western Blotting: Western blots were developed by ECL (PIERCE).

Results

A yeast 2 hybrid screening was effected using intact NIK cDNA (GenBank Accession No. Y10256; SEQ ID NO: 5), NIK-C-terminus (amino acids 624-947 of SEQ ID NO: 5) or NIK-N terminus (amino acids 1-367) as a prey. The most prevalent prey which was found in these screenings was the α7 subunit (HC8) (GenBank Accession No. XM_050947). These interactions were validated in the heterologous yeast strain, SFY526, wherein the HC8 interactions with NIK-C terminus or with NIK-N terminus were found substantially much stronger than the HC8 interaction with full length NIK (see Table 1, below).

TABLE 1

| Bait | Prey | Strength of Interaction |
| --- | --- | --- |
| NIK | HC8 | ++ |
| NIK | TRAF2 | − |
| NIK-C-ter | HC8 | ++++ |
| NIK-C-ter | TRAF2 | + |
| NIK-N-ter | HC8 | +++ |
| NIK-N-ter | TRAF2 | − |

"++++" and "++" designate the development of strong color (β-gal expression) within 30 minutes and 1 h following assay initiation, respectively; "+" indicates the development of strong color following 3 h following assay initiation; "−" designates no development of color within 24 h following assay initiation.

Figure 1:
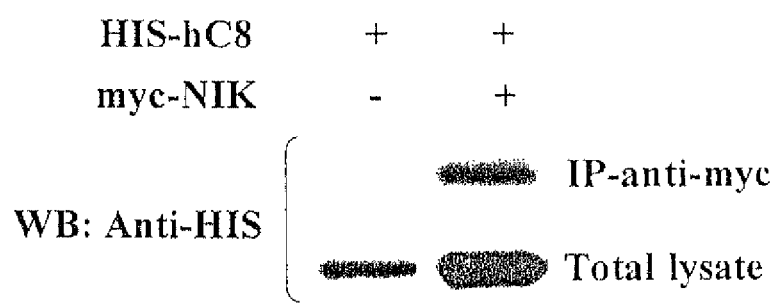
FIG. 1 shows Western blot analysis of immunoprecipitation assays illustrating an interaction between NIK and HC8 in 293T cells transiently transfected therewith. Figure shows the presence of HC8 in a NIK immunocomplex. Lower panel are total cell lysates showing increased levels of HC8 expression in 293T cells co-transfected with NIK.

To address the NIK-HC8 interaction in mammalian cells, a co-immunoprecipitation assay was effected in lysates of 293T cells transiently co-expressing NIK (Accession No. Y10256; SEQ ID NO:5) and/or HC8 (Accession No. XM_050947). As is evident from FIGS. 1a-b, co-immunoprecipitation experiments show that NIK and HC8 interact in a bidirectional manner, namely, immunoprecipitating NIK co-precipitated HC8 (FIG. 1), while immunoprecipitating HC8 co-precipitated NIK. An aly mutation in NIK [which causes an amino acid substitution in the C-terminus of NIK (Shikura (1999) Nat. Genet. 22:74-7] completely abolished interaction thereof with HC8. In addition, mouse NIK was found to be capable of binding to HC8 (FIG. 6).

Figure 3A:
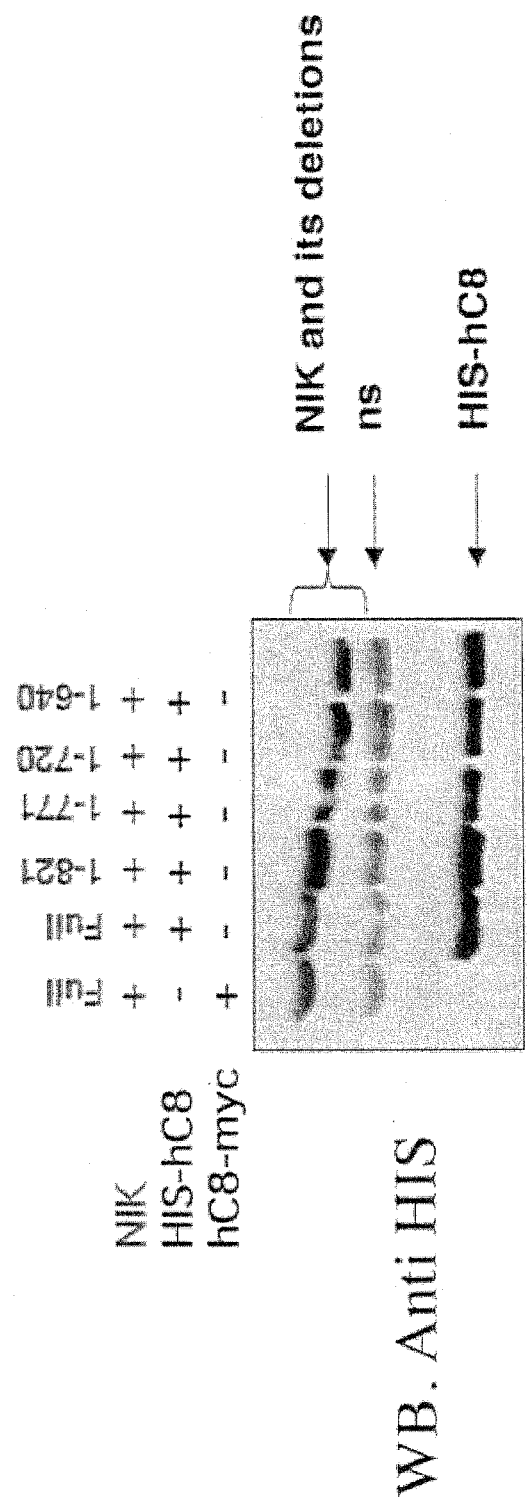
FIGS. 3a-g show deletion analyses of a human NIK region which binds to HC8. Full-length NIK and various deletion mutants thereof (with the indicated N- and C-terminal residues), linked to the His tag, were transiently co-expressed in HeLa cells with HC8 fused either to the His or Myc tag and their association was assessed by immunoprecipitation of NIK from the cell lysates using anti-NIK or anti-HIS monoclonal antibody followed by Western analysis.
Figures 3B, 3C:
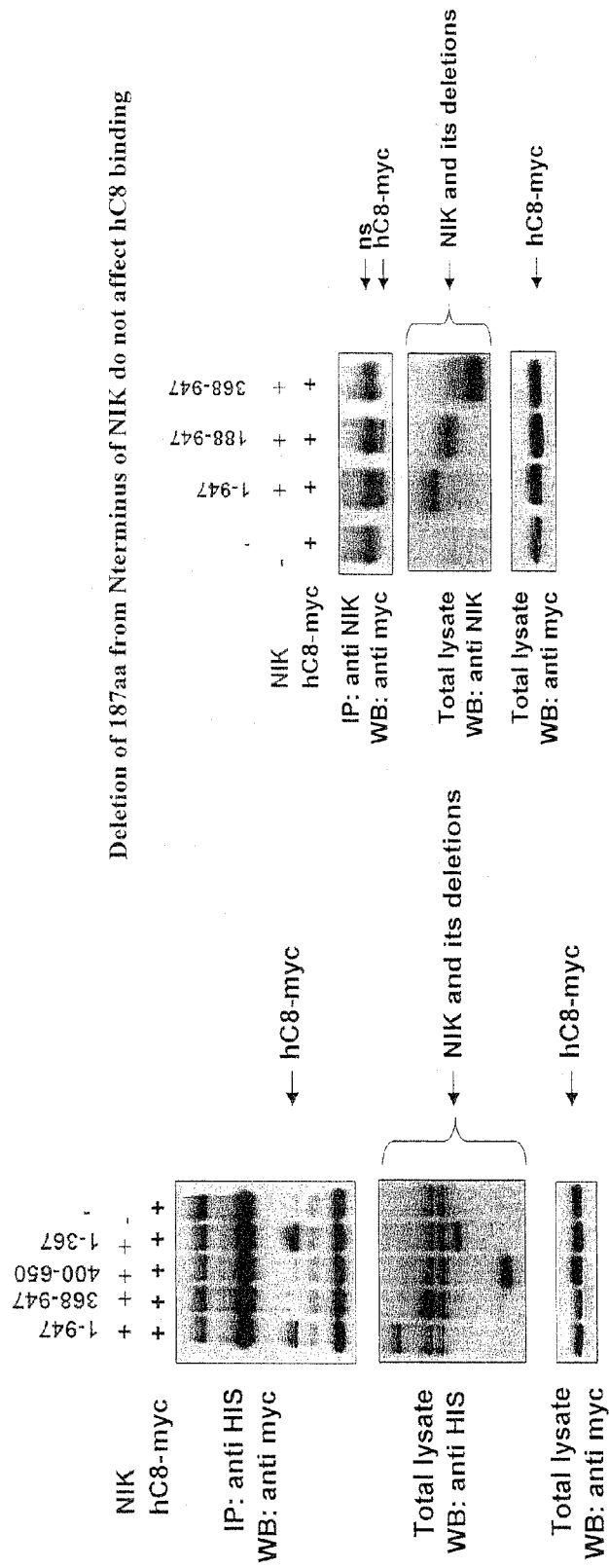
Figure 3D:
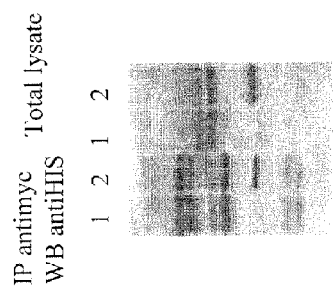
Figure 3E:
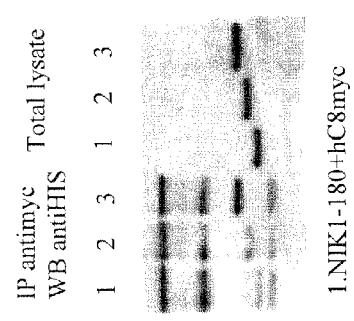
Figure 3G:
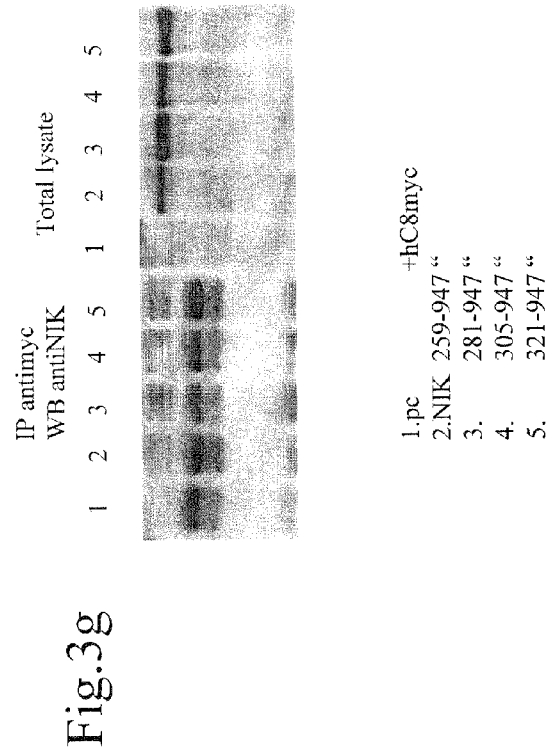
Figure 3F:
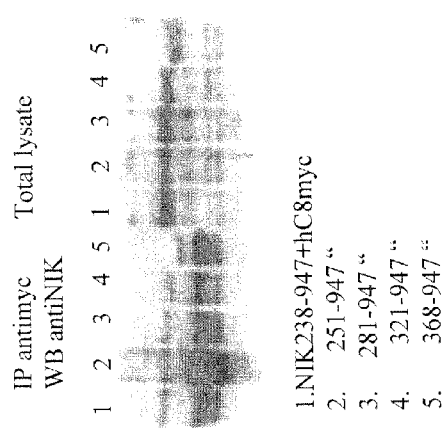

Deletion analyses of human NIK revealed the presence of at least two HC8-binding regions: one within amino acids 650-947 at the C-terminus of NIK (FIG. 3a), and another within the amino acids 1-180 at the N-terminus of NIK (FIGS. 3b-c, 4).

Co-immunoprecipitation experiments using Myc-tagged HC8 and His-tagged NIK transiently co-expressed in HeLa cells show that the NIK-HC8 binding occurs within the proteasome-associated HC8 (as opposed to free HC8; FIG. 5). An aly mutation, replacement of lysine 670 with alanine, or a naturally occurring single nucleotide polymorphic variation of NIK (H674Y) did not affect NIK binding to the proteasome-associated HC8 (FIG. 7).

Example 2

NIK Phosphorylates HC8 at Two Serine Residues in its C-Terminus

HC8 contains two conserved serine residues, S243 and S250, which are targets for casein kinase 2 (CK2) phosphorylation (Castano et al., Biochemistry 35:3782-789, 1996). In order to test the capacity of NIK to phosphorylate HC8, an in-vitro kinase assay was effected.

Materials and Experimental Procedures

In vitro kinase assay and Western blotting were performed essentially as described by Ramakrishnan et al. (Immunity 21: 477-489, 2004).

Results

As is shown in FIGS. 2a-b, HC8 was found to be a substrate for NIK phosphorylation in an in vitro kinase assay. Replacement of two serine residues on HC8 (amino acids 243 and 250) by alanine completely abolished the NIK-induced phosphorylation of HC8 (FIG. 2a). However, while the HC8 mutant was bound to NIK (similarly to the wild type HC8) it was not bound to aly NIK (FIG. 2b).

As shown in FIG. 8, mutation of serine residues 243 and 250 of HC8 substantially inhibited NIK-induced alternative NF-κB pathway as well as nuclear translocation of HC8 and NIK. The data further 8 suggests that the NIK induced phosphorylation of HC8 which results from the NIK-HC8 binding may serve to enhance NIK degradation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications and GenBank Accession numbers mentioned in this specification are herein incorporated in their entirety by reference into the specification, to the same extent as if each individual publication, patent or patent application or GenBank Accession Number was specifically and individually indicated to be incorporated herein by reference. In addition, citation or identification of any reference in this application shall not be construed as an admission that such reference is available as prior art to the present invention.

What is claimed is:

1. An isolated polypeptide consisting of no more than 200 amino acids and comprising the amino acid sequence set forth by amino acids 1-180 of SEQ ID NO: 5 (human NIK), the isolated polypeptide being capable of disrupting a human NIK-HC8 complex or preventing formation thereof.

2. A composition comprising the polypeptide of claim 1.

* * * * *

SEQUENCE LISTING

<160> NUMBER OF SEQ ID NOS: 5

<210> SEQ ID NO 1
<211> LENGTH: 21
<212> TYPE: DNA
<213> ORGANISM: Artificial
<220> FEATURE:
<223> OTHER INFORMATION: Synthetic SiRNA oligonucleotide

<400> SEQUENCE: 1
uaccuccacu cacgaaggat t                                              21

<210> SEQ ID NO 2
<211> LENGTH: 21
<212> TYPE: DNA
<213> ORGANISM: Artificial
<220> FEATURE:
<223> OTHER INFORMATION: Synthetic SiRNA oligonucleotide

<400> SEQUENCE: 2
uaccuccacu cacgaaggat t                                              21

<210> SEQ ID NO 3
<211> LENGTH: 21
<212> TYPE: DNA
<213> ORGANISM: Artificial
<220> FEATURE:
<223> OTHER INFORMATION: Synthetic SiRNA oligonucleotide

<400> SEQUENCE: 3
gcagaaugcc ucccaggaut t                                              21

<210> SEQ ID NO 4
<211> LENGTH: 21
<212> TYPE: DNA
<213> ORGANISM: Artificial
<220> FEATURE:
<223> OTHER INFORMATION: Synthetic SiRNA oligonucleotide

<400> SEQUENCE: 4
auccugggag gcauucugct t                                              21

<210> SEQ ID NO 5
<211> LENGTH: 947
<212> TYPE: PRT
<213> ORGANISM: Homo sapiens

<400> SEQUENCE: 5

Met Ala Val Met Glu Met Ala Cys Pro Gly Ala Pro Gly Ser Ala Val
1               5                   10                  15

Gly Gln Gln Lys Glu Leu Pro Lys Pro Lys Glu Lys Thr Pro Pro Leu
            20                  25                  30

Gly Lys Lys Gln Ser Ser Val Tyr Lys Leu Glu Ala Val Glu Lys Ser
        35                  40                  45

Pro Val Phe Cys Gly Lys Trp Glu Ile Leu Asn Asp Val Ile Thr Lys
    50                  55                  60

Gly Thr Ala Lys Glu Gly Ser Glu Ala Gly Pro Ala Ala Ile Ser Ile
65                  70                  75                  80

Ile Ala Gln Ala Glu Cys Glu Asn Ser Gln Glu Phe Ser Pro Thr Phe
                85                  90                  95

Ser Glu Arg Ile Phe Ile Ala Gly Ser Lys Gln Tyr Ser Gln Ser Glu
            100                 105                 110

```
Ser Leu Asp Gln Ile Pro Asn Asn Val Ala His Ala Thr Glu Gly Lys
        115                 120                 125

Met Ala Arg Val Cys Trp Lys Gly Lys Arg Ser Lys Ala Arg Lys
    130                 135                 140

Lys Arg Lys Lys Lys Ser Ser Lys Ser Leu Ala His Ala Gly Val Ala
145                 150                 155                 160

Leu Ala Lys Pro Leu Pro Arg Thr Pro Glu Gln Glu Ser Cys Thr Ile
                165                 170                 175

Pro Val Gln Glu Asp Glu Ser Pro Leu Gly Ala Pro Tyr Val Arg Asn
            180                 185                 190

Thr Pro Gln Phe Thr Lys Pro Leu Lys Glu Pro Gly Leu Gly Gln Leu
        195                 200                 205

Cys Phe Lys Gln Leu Gly Glu Gly Leu Arg Pro Ala Leu Pro Arg Ser
    210                 215                 220

Glu Leu His Lys Leu Ile Ser Pro Leu Gln Cys Leu Asn His Val Trp
225                 230                 235                 240

Lys Leu His His Pro Gln Asp Gly Gly Pro Leu Pro Leu Pro Thr His
                245                 250                 255

Pro Phe Pro Tyr Ser Arg Leu Pro His Pro Phe Pro Phe His Pro Leu
            260                 265                 270

Gln Pro Trp Lys Pro His Pro Leu Glu Ser Phe Leu Gly Lys Leu Ala
        275                 280                 285

Cys Val Asp Ser Gln Lys Pro Leu Pro Asp Pro His Leu Ser Lys Leu
    290                 295                 300

Ala Cys Val Asp Ser Pro Lys Pro Leu Pro Gly Pro His Leu Glu Pro
305                 310                 315                 320

Ser Cys Leu Ser Arg Gly Ala His Glu Lys Phe Ser Val Glu Glu Tyr
                325                 330                 335

Leu Val His Ala Leu Gln Gly Ser Val Ser Ser Gln Ala His Ser
            340                 345                 350

Leu Thr Ser Leu Ala Lys Thr Trp Ala Ala Arg Gly Ser Arg Ser Arg
        355                 360                 365

Glu Pro Ser Pro Lys Thr Glu Asp Asn Glu Gly Val Leu Leu Thr Glu
    370                 375                 380

Lys Leu Lys Pro Val Asp Tyr Glu Tyr Arg Glu Glu Val His Trp Ala
385                 390                 395                 400

Thr His Gln Leu Arg Leu Gly Arg Gly Ser Phe Gly Glu Val His Arg
                405                 410                 415

Met Glu Asp Lys Gln Thr Gly Phe Gln Cys Ala Val Lys Lys Val Arg
            420                 425                 430

Leu Glu Val Phe Arg Ala Glu Glu Leu Met Ala Cys Ala Gly Leu Thr
        435                 440                 445

Ser Pro Arg Ile Val Pro Leu Tyr Gly Ala Val Arg Glu Gly Pro Trp
    450                 455                 460

Val Asn Ile Phe Met Glu Leu Leu Glu Gly Gly Ser Leu Gly Gln Leu
465                 470                 475                 480

Val Lys Glu Gln Gly Cys Leu Pro Glu Asp Arg Ala Leu Tyr Tyr Leu
                485                 490                 495

Gly Gln Ala Leu Glu Gly Leu Glu Tyr Leu His Ser Arg Arg Ile Leu
            500                 505                 510

His Gly Asp Val Lys Ala Asp Asn Val Leu Leu Ser Ser Asp Gly Ser
        515                 520                 525

His Ala Ala Leu Cys Asp Phe Gly His Ala Val Cys Leu Gln Pro Asp
```

```
                530                 535                 540
Gly Leu Gly Lys Ser Leu Leu Thr Gly Asp Tyr Ile Pro Gly Thr Glu
545                 550                 555                 560

Thr His Met Ala Pro Glu Val Val Leu Gly Arg Ser Cys Asp Ala Lys
                565                 570                 575

Val Asp Val Trp Ser Ser Cys Cys Met Met Leu His Met Leu Asn Gly
                580                 585                 590

Cys His Pro Trp Thr Gln Phe Phe Arg Gly Pro Leu Cys Leu Lys Ile
            595                 600                 605

Ala Ser Glu Pro Pro Pro Val Arg Glu Ile Pro Ser Cys Ala Pro
        610                 615                 620

Leu Thr Ala Gln Ala Ile Gln Glu Gly Leu Arg Lys Glu Pro Ile His
625                 630                 635                 640

Arg Val Ser Ala Ala Glu Leu Gly Gly Lys Val Asn Arg Ala Leu Gln
                645                 650                 655

Gln Val Gly Gly Leu Lys Ser Pro Trp Arg Gly Glu Tyr Lys Glu Pro
                660                 665                 670

Arg His Pro Pro Pro Asn Gln Ala Asn Tyr His Gln Thr Leu His Ala
            675                 680                 685

Gln Pro Arg Glu Leu Ser Pro Arg Ala Pro Gly Pro Arg Pro Ala Glu
        690                 695                 700

Glu Thr Thr Gly Arg Ala Pro Lys Leu Gln Pro Leu Pro Pro Glu
705                 710                 715                 720

Pro Pro Glu Pro Asn Lys Ser Pro Pro Leu Thr Leu Ser Lys Glu Glu
                725                 730                 735

Ser Gly Met Trp Glu Pro Leu Pro Leu Ser Ser Leu Glu Pro Ala Pro
            740                 745                 750

Ala Arg Asn Pro Ser Ser Pro Glu Arg Lys Ala Thr Val Pro Glu Gln
        755                 760                 765

Glu Leu Gln Gln Leu Glu Ile Glu Leu Phe Leu Asn Ser Leu Ser Gln
770                 775                 780

Pro Phe Ser Leu Glu Glu Gln Glu Gln Ile Leu Ser Cys Leu Ser Ile
785                 790                 795                 800

Asp Ser Leu Ser Leu Ser Asp Ser Glu Lys Asn Pro Ser Lys Ala
                805                 810                 815

Ser Gln Ser Ser Arg Asp Thr Leu Ser Ser Gly Val His Ser Trp Ser
            820                 825                 830

Ser Gln Ala Glu Ala Arg Ser Ser Trp Asn Met Val Leu Ala Arg
        835                 840                 845

Gly Arg Pro Thr Asp Thr Pro Ser Tyr Phe Asn Gly Val Lys Val Gln
850                 855                 860

Ile Gln Ser Leu Asn Gly Glu His Leu His Ile Arg Glu Phe His Arg
865                 870                 875                 880

Val Lys Val Gly Asp Ile Ala Thr Gly Ile Ser Ser Gln Ile Pro Ala
                885                 890                 895

Ala Ala Phe Ser Leu Val Thr Lys Asp Gly Gln Pro Val Arg Tyr Asp
            900                 905                 910

Met Glu Val Pro Asp Ser Gly Ile Asp Leu Gln Cys Thr Leu Ala Pro
        915                 920                 925

Asp Gly Ser Phe Ala Trp Ser Trp Arg Val Lys His Gly Gln Leu Glu
        930                 935                 940

Asn Arg Pro
945
```